United States Patent [19]
Wilk

[11] Patent Number: 5,730,722
[45] Date of Patent: *Mar. 24, 1998

[54] METHOD AND APPARATUS FOR SUPPLYING A MEDICAL TREATMENT COMPOSITION TO A PATIENT

[76] Inventor: Peter J. Wilk, 185 West End Ave., New York, N.Y. 10023

[ * ] Notice: The term of this patent shall not extend beyond the expiration date of Pat. No. 5,318,519.

[21] Appl. No.: 195,919

[22] Filed: Feb. 10, 1994

Related U.S. Application Data

[63] Continuation-in-part of Ser. No. 932,368, Aug. 19, 1992, Pat. No. 5,318,519.

[51] Int. Cl.⁶ .................................................. A61M 5/00
[52] U.S. Cl. ........................ 604/52; 604/151; 604/891.1; 128/899
[58] Field of Search .................. 604/49, 50, 52, 604/53, 65, 93, 151, 175, 891.1; 128/899, DIG. 12; 623/66

[56] References Cited

U.S. PATENT DOCUMENTS

| | | | |
|---|---|---|---|
| 4,146,029 | 3/1979 | Ellinwood, Jr. | 604/891.1 |
| 4,315,513 | 2/1982 | Nawash et al. | 604/175 |
| 4,335,711 | 6/1982 | Olsen | 604/83 |
| 4,344,435 | 8/1982 | Aubin | 604/175 |
| 4,354,933 | 10/1982 | Lester | 604/5 |
| 4,525,165 | 6/1985 | Fischell | 604/891.1 |
| 4,573,994 | 3/1986 | Fischell et al. | 604/891.1 |
| 4,588,407 | 5/1986 | Isono et al. | 623/66 |
| 4,596,575 | 6/1986 | Rosenberg et al. | 604/891.1 |
| 4,681,560 | 7/1987 | Schulte et al. | 604/9 |
| 4,687,468 | 8/1987 | Gianturco | 604/9 |
| 4,714,462 | 12/1987 | DiDomenico | 604/891.1 |
| 4,822,337 | 4/1989 | Newhouse et al. | 604/50 |
| 4,826,810 | 5/1989 | Aoki | 604/151 |
| 4,908,012 | 3/1990 | Moise et al. | 604/151 |
| 4,911,168 | 3/1990 | Davis | 604/50 |
| 4,927,407 | 5/1990 | Dorman | 600/16 |
| 5,069,662 | 12/1991 | Bodden | 604/4 |
| 5,217,460 | 6/1993 | Knoepfler | 606/205 |
| 5,318,519 | 6/1994 | Wilk | 604/52 |

FOREIGN PATENT DOCUMENTS

| 355591 | 2/1990 | European Pat. Off. | 604/891.1 |
|---|---|---|---|

OTHER PUBLICATIONS

Blackshear, *Implantable Drug Delivery Systems*, Scientific American, Dec. 1979, pp. 66–73.

*Primary Examiner*—Michael Buiz
*Assistant Examiner*—Nancy Mulcare
*Attorney, Agent, or Firm*—Henry D. Coleman; R. Neil Sudol

[57] ABSTRACT

In a therapeutic medical method, a pump and a container are surgically inserted into a patient's abdominal cavity so that the pump is operatively connected to an outlet of the container. The outlet is surgically connected to a selected organ in the abdominal cavity of the patient so that the container can communicate with the organ via the outlet. Subsequently, the pump is operated to move a medical treatment composition from the container to the selected organ in accordance with a first delivery schedule. The progress of the patient is monitored during a period of treatment of the organ at the first delivery schedule, and subsequently, in response to information which is acquired during the step of monitoring and which concerns an effect on the patient of the first treatment schedule, the pump is operated to move the medical treatment composition from the container to the organ in accordance with a second delivery schedule different from the first.

10 Claims, 2 Drawing Sheets

METHOD AND APPARATUS FOR SUPPLYING A MEDICAL TREATMENT COMPOSITION TO A PATIENT

CROSS-REFERENCE TO A RELATED APPLICATION

This application is a continuation-in-part of U.S. patent application Ser. No. 07/932,368 filed Aug. 19, 1992, now U.S. Pat. No. 5,318,519.

BACKGROUND OF THE INVENTION

This invention relates to a method for supplying a medical treatment composition to a patient and particularly to a predetermined internal organ of the patient such as the liver or the urinary bladder. This invention also relates to an apparatus for carrying out the method.

Chemotherapy is a technique which is widely used in the treatment of cancer. The technique involves the delivery of a molecular composition to a target region or organ of the patient at such a dosage rate as to destroy the malignant cells. A great proportion of the expense in conventional chemotherapy arises from the treatment of the patient in a hospital. A chemotherapeutic method which reduced the frequency and/or duration of hospital visits would also substantially reduce overall costs of chemotherapy.

OBJECTS OF THE INVENTION

An object of the present invention is to provide a new method for chemotherapeutic treatments.

Another object of the present invention is to provide such a new chemotherapeutic procedure which substantially reduces overall costs of chemotherapy.

Another, more particular, object of the present invention is to provide such a new chemotherapeutic procedure which reduces the frequency and/or duration of hospital visits.

A further object of the present invention is to provide a new device for use in such a chemotherapeutic procedure.

These and other objects of the present invention will be apparent from the drawings and detailed descriptions herein.

SUMMARY OF THE INVENTION

A therapeutic medical method comprises, in accordance with the present invention, the steps of (a) providing a pump and a container having an inlet and an outlet, (b) surgically inserting the container and the pump into a patient's abdominal cavity so that the pump is operatively connected to the outlet, (c) surgically connecting the outlet to a selected organ in the abdominal cavity of the patient so that the container can communicate with the organ via the outlet, and (d) upon completion of the steps of inserting and connecting, operating the pump to move a medical treatment composition from the container to the selected organ in accordance with a first delivery schedule. The progress of the patient is monitored during a period of treatment of the organ at the first delivery schedule. Subsequently, in response to information which is acquired during the step of monitoring and which concerns an effect on the patient of the first treatment schedule, the pump is operated to move the medical treatment composition from the container to the organ in accordance with a second delivery schedule different from the first.

Each delivery schedule is characterized by a pumping rate. In addition, inasmuch as the pump may be operated intermittently, each delivery schedule is characterized by the periods of operation, as well as the times between operating periods.

According to another feature of the present invention, a control unit is implanted into the abdominal cavity of the patient and connected to the pump. The method further comprises the step, implemented at the end of the period of treatment, of transmitting a control signal from outside the patient to the control unit. The operation of the pump subsequent to the monitoring step includes the step of operating the pump via the control unit in accordance with the control signal.

The medical treatment composition may take the form of a chemotherapeutic composition delivered, for example, to a selected vein in the portal vein system so that the container communicates with the liver. Alternatively, the chemotherapeutic agent may be delivered to the urinary bladder or another internal organ of the patient.

Where the container is provided with a power source for energizing the pump, the method further comprises the step of charging the power source from a power supply outside the patient's body. The power source may be connected to the power supply via a lead extending through the abdominal wall of the patient.

To accommodate large amounts of a fluidic treatment composition, it is contemplated that the container or reservoir is disposed to rest on the pelvic rim.

Generally, the container or reservoir will be refilled one or more times during a series of successive treatment schedules. Sometimes, it may be desirable to provide a different medical treatment composition. Accordingly, the method contemplates the additional steps of providing a port in an abdominal wall of the patient, connecting the inlet to the port, and feeding a supply of the medical treatment composition to the container via the port and the inlet.

An apparatus for supplying a medical-treatment composition to a patient comprises, in accordance with the present invention, a container disposed in the patient's abdominal cavity and having an inlet port and an outlet port, the inlet port being connected to a port component disposed in the patient's abdominal wall, the outlet port being connected to an internal organ of the patient in the abdominal cavity. A pump is disposed in the patient's abdominal cavity and is operatively connected to the container for pumping the medical treatment composition from the container to the internal organ of the patient. A control unit is disposed in the abdominal cavity and is operatively connected to the pump for controlling times and speeds of operation of the the pump. In addition, means such as a circuit is operatively connected to the control unit for changing a delivery schedule of the medical treatment composition from the container to the internal organ.

Where the pump includes a power source, the apparatus further comprises means, such as a lead extending from the power source to the port component, for enabling a periodic recharging of the power source.

A particular therapeutic medical method comprises, in accordance with the present invention, the steps of (i) providing a pump and a container having an inlet and an outlet, (ii) surgically inserting the container and the pump into a patient's abdominal cavity so that the pump is operatively connected to the outlet, (iii) surgically connecting the outlet to a urinary bladder of the patient so that the container can communicate with the bladder via the outlet, and (iv) subsequetly operating the pump to move a medical treatment composition from the container to the urinary bladder.

The container or reservoir, as well as the pump and connecting conduits and wiring, may be inserted laparoscopically into the abdominal cavity of the patient.

The present invention provides a new method for chemotherapeutic treatment. Such a method substantially reduces overall costs of chemotherapy. The frequency and/or duration of hospital visits is reduced.

DETAILED DESCRIPTION

Figure 1:
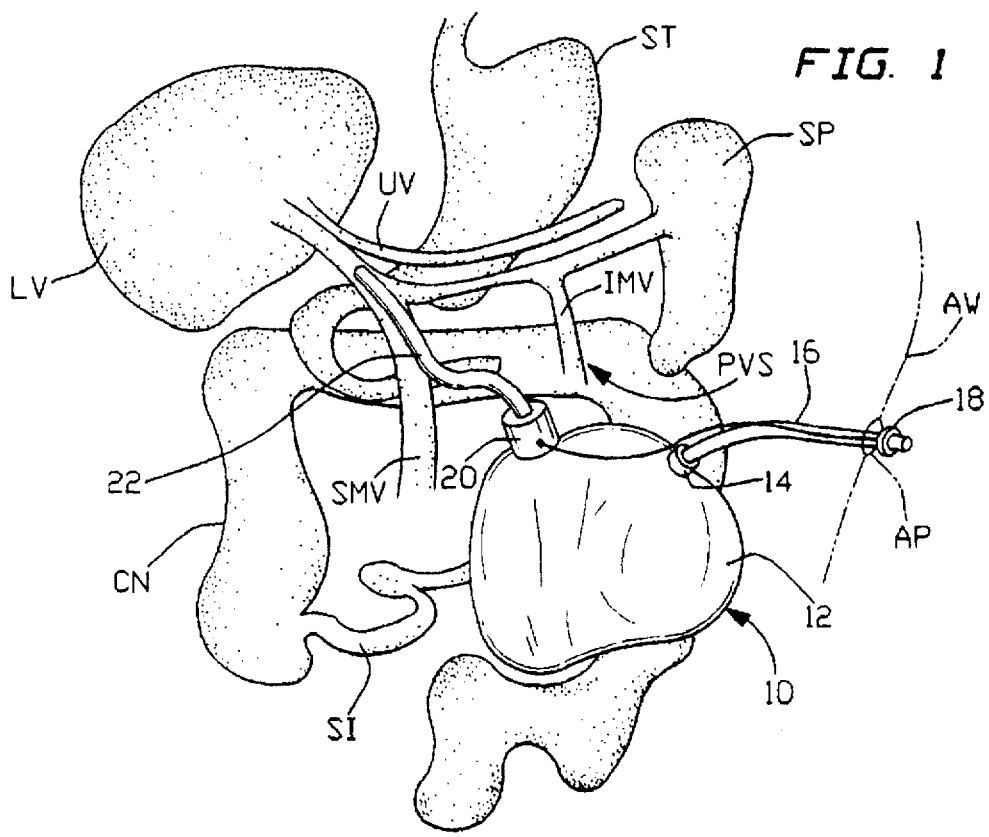
FIG. 1 is a diagram of abdominal organs of a patient, schematically showing a reservoir implanted into a patient's abdominal cavity for containing a nutritional composition of a chemotherapeutic treatment composition in accordance with the present invention.

As illustrated in FIG. 1, an individual's abdominal organs include the stomach ST, the liver LV, the spleen SP, the colon CN, the small intestine SI and the portal vein system PVS. The portal vein system PVS includes blood vessels which extend from the intestines CN and SI to the liver for delivering thereto nutrient carrying blood for processing by the liver LV. The portal vein system PVS includes the superior mesenteric vein SMV, the inferior mesenteric vein IMV, the spleen vein SV and the umbilical vein UV.

As further illustrated in FIG. 1, an assembly 10 for supplying total parenteral nutrition or a chemotherapeutic composition for the treatment of liver cancer has been surgically implanted into the abdomen. Assembly 10 basically comprises a reservoir or container 12 which is implanted to rest on the pelvic rim PR (see FIG. 4).

Container 12 has an inlet port 14 which is surgically connected via a tube or conduit 16 to a port component 18 disposed in the abdominal wall AW of the patient. A pump 20 is mounted to container 12 at an outlet thereof. A tube or outlet conduit 22 extends from pump 20 to the superior mesenteric vein SMV where the distal end of the outlet conduit has been surgically inserted.

It is to be noted that outlet conduit 22 may be connected at its distal end to virtually any vein of the portal vein system, including, but not limited, to the superior mesenteric vein, the inferior mesenteric vein and the spleen vein.

As mentioned above, container 12 may hold a supply of a liquid nutritive solution for feeding by pump 20 directly into the portal vein system and from thence to the liver. The feeding of the liquid nourishment to the portal vein system is considered more efficient than the conventional feeding to a vein in the chest inasmuch as nutritive substances need not be carried around the body prior to extraction by the liver for processing.

The use of the implanted container or reservoir 12 and its attendant hardware for supplying a chemotherapeutic composition to the liver LV serves to reduce hospitalization times and associated expense. Treatment can be extended over a substantial period without a need for the patient to continually visit a hospital during the period. The patient's progress can be monitored at the end of a treatment period or periodically on an out-patient basis during the treatment period.

Figure 4:
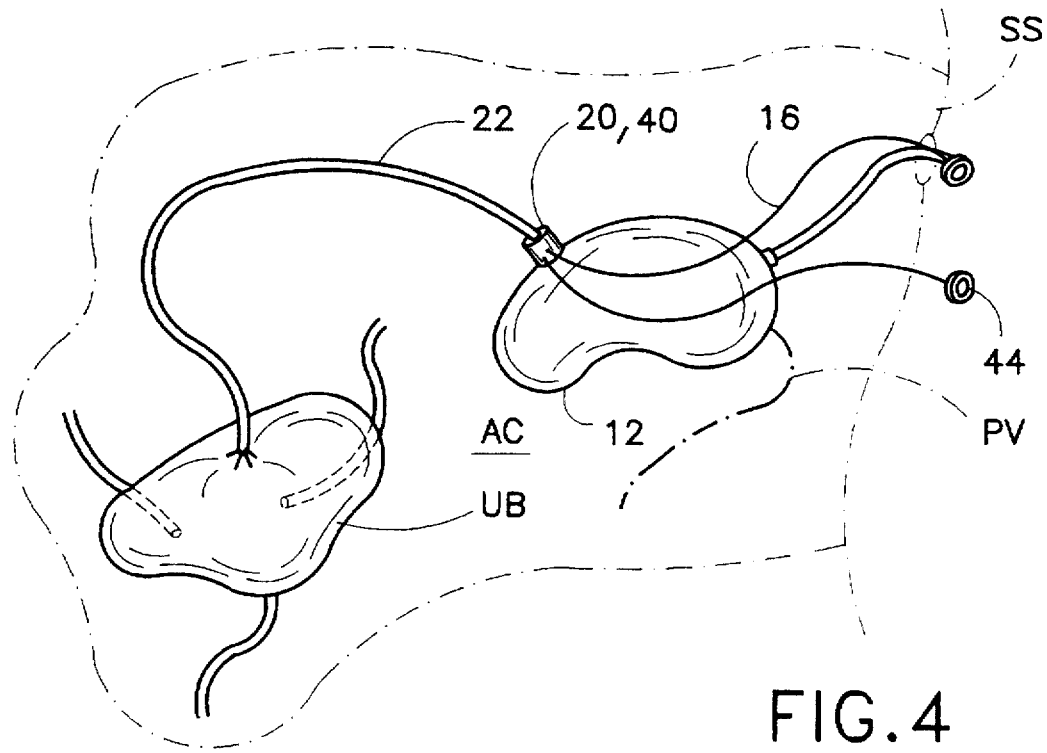
FIG. 4 is a diagram of an abdominally implanted chemotherapeutic reservoir in accordance with the present invention, showing connection of the reservoir to a urinary bladder of a patient.

Container 12 is surgically inserted into the abdominal cavity AC of the patient so that the container rests on pelvic rim PV (see FIG. 4). The disposition of container 12 may be effectuated through open surgery or laparoscopically. In the latter technique, container 12 must be of sufficient flexibility to permit collapse and folding into a configuration small enough to fit down a laparoscopic cannula or trocar sleeve. Upon insertion of the collapsed bag into the abdomen, the bag is opened and positioned, via the use of laparoscopic graspers.

Container 12 is accordingly made of a flexible biocompatible material such as silicone or a nonbioabsorbable polymeric composition.

An outlet of container 12 (at pump 20) is surgically connected to a selected vein in the portal vein system PVS so that container 12 communicates with liver LV via the container outlet and the selected vein. The connection of outlet conduit 22 to the portal vein system PVS may be implemented after the disposition of container 12 in the abdomen. Alternatively, it is possible to connect conduit 22 first to the portal vein system and subsequently to container 12. In the latter event, it is particularly necessary to test the integrity of the connection of the conduit 22 to container 12, or to pump 20, to ensure that liquid from container 12 does not leak into the abdomen. In fact, the entire nutrient or chemotherapeutic delivery system should be tested after installation to ensure the integrity of all lines and connections. During such testing, pump 20 is operated to move liquid from container 12 to the selected vein in the portal vein system PVS.

During the surgical implantation procedure, port component 18 is positioned in an aperture AP formed in the abdominal wall AW and is connected to inlet port 14 via tube or conduit 16. Upon the disposition of container 12 in the abdomen and the connection of the container to port component 18 via inlet conduit 16, port component 18 may be connected to an external supply of a liquid nutrient or chemical composition (not shown). The liquid is fed from the external supply to container 12 via port component 18, inlet conduit 16 and inlet port 14. This feeding, which may take place periodically after the completion of the operation in order to refill container or reservoir 12, should be tested prior to the completion of the implantation operation to ensure effective system operation.

Figure 2:
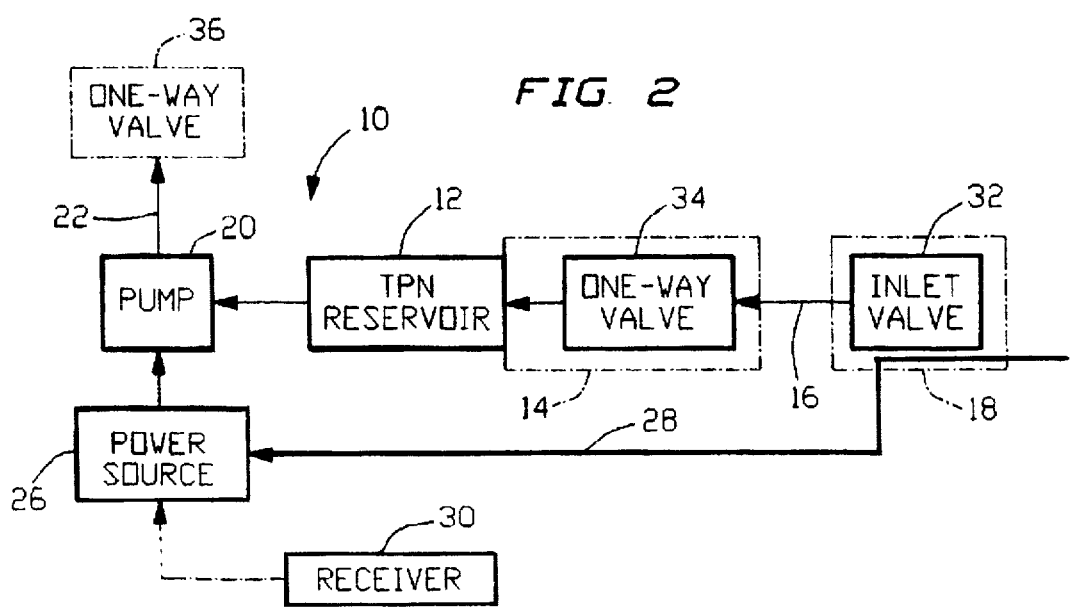
FIG. 2 is a block diagram of operative components of an implanted nutrition reservoir assembly as shown in FIG. 1.

As illustrated in FIG. 2, container 12 is provided with a power source 26 operatively connected to pump 20 for energizing the pump. Power source 26 may be periodically energized or charged from a power supply (not shown) outside the patient's body. The charging of power source 26 may be effectuated by connecting power source 26 to the external power supply via a lead 28 extending through the abdominal wall AW of the patient. More particularly, lead 28 extends to port component 18 where an electrical contact may be formed. Alternatively, pump 20 is connected to a wireless energy receiver 30 which is attached to container 12 and which functions to extract power from an incoming wireless beam of electromagnetic or magnetic radiation.

Upon completion of implantation, a user of parenteral nutrition may periodically connect port component 18 to an external supply of a liquid nutrient for purposes of replenishing the supply in reservoir or container 12. Upon a disconnection of the external supply from port component 18, the port component is closed (e.g., with a cap, not illustrated). Upon the filling of container 12, an amount of the nutritive composition is continuously or periodically pumped by pump 20 from container 12 to the patient's liver LV via the portal vein system PVS.

Figure 3:
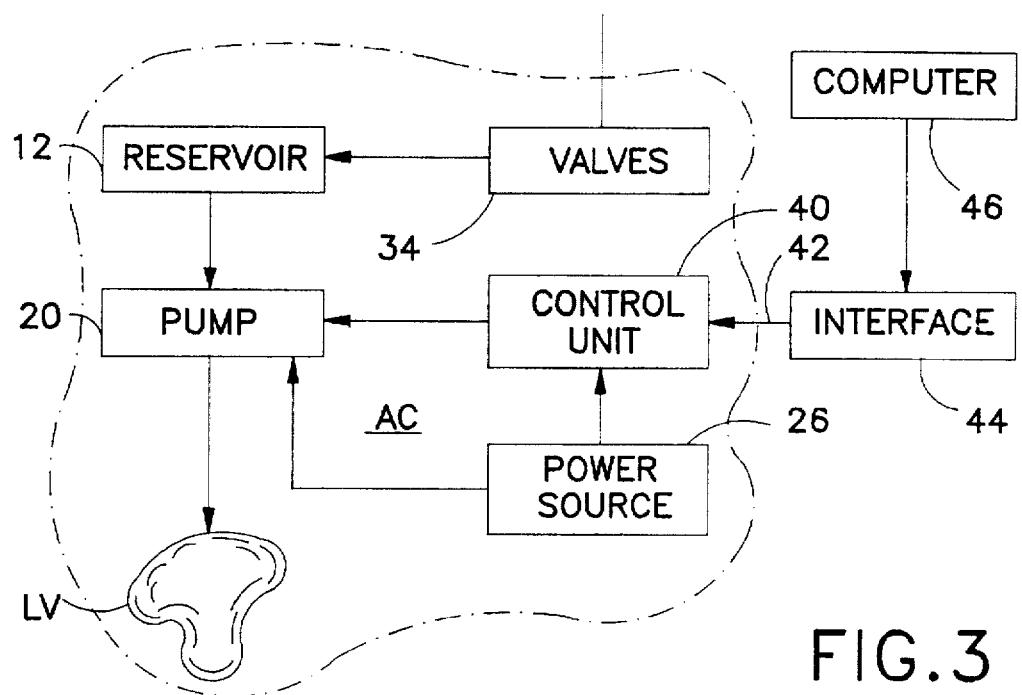
FIG. 3 is a block diagram illustrating operative components of an implanted chemotherapeutic reservoir assembly having the configuration shown in FIG. 1.

As further illustrated in FIG. 2, the liquid delivery or supply assembly 10 further includes an inlet valve 32 at port component 18 and another one-way valve 34 at inlet port 14. A one-way valve 36 may additionally be provided in the output line extending to the portal vein system PVS.

Where container 12 is disposed in a cancer patient's abdomen for purposes of subjecting that patient to chemotherapy, it is contemplated that the operating rate or speed of pump 20, as well as its times of operaton, is determined by signals from an implanted control unit or programmer 40 diagrammatically depicted in FIG. 3. Control unit 40 is energized by power source 26 and is connected via a lead or multiple 42 to an interface, electrical port or coupling 44 disposed at a skin surface SS of the patient, for example, an adbominal skin surface. A computer or other reprogramming unit 46 is connectable to control unit 40 via interface 44 for changing the operating speed and other characteristics of an operating cycle, such as the times of operation and durations of inactivity.

Upon completed insertion of container 12 into a patient and connection of the container to liver LV (FIG. 1), pump 20 is controlled by unit 40 to move a chemotherapeutic treatment composition from container 12 to liver LV in accordance with a first predetermined delivery schedule. The progress of the patient is monitored during a period of treatment of liver LV at the first delivery schedule (including periodically or at the end of the treatment period). Subsequently, in response to information which is acquired by the monitoring and which concerns an effect on the patient of the first treatment schedule, computer 46 is connected via interface 44 to control unit 40 to transmit thereto a control signal for changing the treatment schedule (pumping rate, etc.). Pump 20 is then operated to move the chemotherapeutic treatment composition from container 12 to liver LV in accordance with the second delivery schedule. Generally, the second treatment schedule is selected in accordance with, i.e., depending on, the results of the first treatment schedule.

FIG. 4 illustrates portions of a chemotherapeutic delivery assembly wherein a chemotherapeutic agent is delivered to the urinary bladder UB of a patient. The assembly of FIG. 4 has the same reference numerals as used in FIG. 1 for the same components.

Generally, container or reservoir 12 will be refilled one or more times during a series of successive chemotherapeutic treatment schedules. Sometimes, it may be desirable to provide a different medical treatment composition. Refilling of container 12 is described above.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A therapeutic medical method, comprising the steps of:
   providing a pump and a container having an inlet and an outlet;
   surgically inserting said container and said pump into a patient's abdominal cavity so that said pump is operatively connected to said container so that said pump can move fluid from said container through said outlet, the inserting of said container and said pump into the patient's abdominal cavity including the step of disposing said container to rest on a pelvic rim of the patient;
   surgically connecting said outlet to a selected organ in the abdominal cavity of the patient so that said container can communicate with the organ via said outlet;
   upon completion of said steps of inserting and connecting, operating said pump to move a medical treatment composition from said container to the selected organ in accordance with a first delivery schedule;
   monitoring said organ during a period of treatment of said organ at said first delivery schedule; and
   in response to information acquired during said step of monitoring regarding an effect on said organ of said first treatment schedule, subsequently operating said pump to move said medical treatment composition from said container to said organ in accordance with a second delivery schedule different from said first delivery schedule.

2. The method defined in claim 1 wherein a control unit is implanted into the abdominal cavity of the patient and connected to said pump, further comprising the step, implemented at the end of said period of treatment, of transmitting a control signal from outside the patient to said control unit, said step of subsequently operating including the step of operating said pump via said control unit in accordance with said control signal.

3. The method defined in claim 1 wherein said medical treatment composition is a cancer treatment composition.

4. The method defined in claim 1 wherein said organ is a selected vein in the portal vein system so that said container communicates with the liver via said outlet and the selected vein of the portal vein system.

5. The method defined in claim 1 wherein said organ is a urinary bladder of the patient.

6. The method defined in claim 1 wherein said container is provided with a power source for energizing the pump, further comprising the step of charging said power source from a power supply outside the patient's body.

7. The method defined in claim 6 wherein said step of charging includes the step of connecting said power source to said power supply via a lead extending through the abdominal wall of the patient.

8. The method defined in claim 1, further comprising the steps of:
   providing a port in an abdominal wall of the patient;
   connecting said inlet to said port; and
   feeding a supply of said medical treatment composition to said container via said port and said inlet.

9. A therapeutic medical method, comprising the steps of:
   providing a pump and a container having an inlet and an outlet;
   surgically inserting said container and said pump into a patient's abdominal cavity so that said pump is operatively connected to said container so that said pump can move fluid from said container through said outlet, the inserting of said container and said pump into the patient's abdominal cavity including the step of disposing said container to rest on a pelvic rim of the patient;
   surgically connecting said outlet to a urinary bladder of the patient so that said container can communicate with the bladder via said outlet; and
   upon completion of said steps of inserting and connecting, operating said pump to move a medical treatment composition from said container to the urinary bladder.

10. The method defined in claim 9 wherein said step of operating said pump includes the step of moving said medical treatment composition from said container to the urinary bladder in accordance with a first delivery schedule, further comprising the steps of monitoring progress of said organ during a period of treatment of said organ at said first delivery schedule, and, in response to information acquired during said step of monitoring regarding an effect on said organ of said first treatment schedule, subsequently operating said pump to move said medical treatment composition from said container to said organ in accordance with a second delivery schedule.

* * * * *